United States Patent [19]

Barlow et al.

[11] 4,117,167
[45] Sep. 26, 1978

[54] DINITROANILINE DERIVATIVES

[75] Inventors: Charles Brian Barlow, Camberley; Peter Frank Hilary Freeman, Reading, both of England

[73] Assignee: Imperial Chemical Industries Limited, London, England

[21] Appl. No.: 556,421

[22] Filed: Mar. 7, 1975

[30] Foreign Application Priority Data

Mar. 7, 1974 [GB] United Kingdom ............... 10241/74
Apr. 11, 1974 [GB] United Kingdom ............... 16171/74
Nov. 6, 1974 [GB] United Kingdom ............... 47976/74

[51] Int. Cl.² .......................... A01N 9/20; C07C 87/54
[52] U.S. Cl. .................................. 424/330; 260/465 E; 260/571; 260/576; 424/304
[58] Field of Search ................. 424/304, 330; 260/576, 260/571

[56] References Cited

U.S. PATENT DOCUMENTS

| | | | |
|---|---|---|---|
| 2,212,825 | 8/1940 | Daudt et al. | 260/571 |
| 3,227,758 | 11/1966 | Richter et al. | 424/330 |
| 3,493,662 | 2/1970 | Duerr | 424/330 |
| 3,562,332 | 2/1971 | Schmidt et al. | 260/576 |
| 3,950,377 | 4/1976 | Barlow | 424/330 X |

FOREIGN PATENT DOCUMENTS 654,690 12/1962 Canada.

Primary Examiner—Allen J. Robinson
Attorney, Agent, or Firm—Cushman, Darby & Cushman

[57] ABSTRACT

Pesticidally active 2-anilino-3,5-dinitrobenzotrifluorides of the formula:

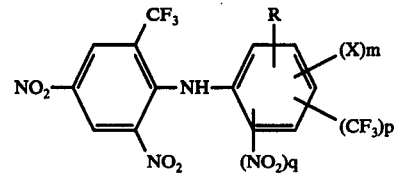

wherein R is hydrogen, methyl or methoxy;
X is halogen,
m is zero, one, two or three,
p is zero, one or two,
q is zero or one and the sum of m, p and q is one, two or three.

10 Claims, No Drawings

DINITROANILINE DERIVATIVES

This invention relates to new compounds, to processes for obtaining them, to compositions comprising them, and to methods of combating pests using them; more particularly to methods of combating insect, acarine and fungal pests of plants.

In Belgium Pat. No. 808,918, there are described 4-anilino benzotrifluoride compounds having pesticidal activity. Surprisingly, we have found greatly improved pesticidal activity in the isomeric 2-anilino benzotrifluoride compounds.

According to the present invention we provide new pesticular dinitrobenzotrifluorides of the general formula:

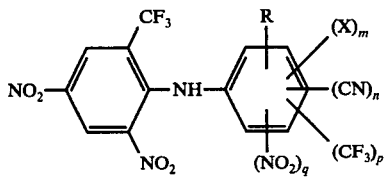

wherein R represents a hydrogen atom or an alkyl or alkoxy group containing up to six carbon atoms; X represents a halogen atom, m is zero or an integer from one to three, n is zero or one, p is zero, one or two and q is zero, one or two, the sum of m,n,p and q being one, two or three; provided that the group

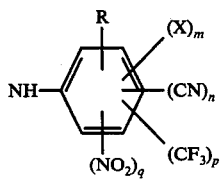

does not represent the 4-cyano-2,6-dinitroanilino group or the 4-trifluoromethyl-2,6-dinitroanilino group. By the term "halogen" as used in this specification and claims is meant fluorine, bromine, chlorine and iodine.

In a preferred aspect the invention provides dinitrobenzotrifluorides of the general formula:

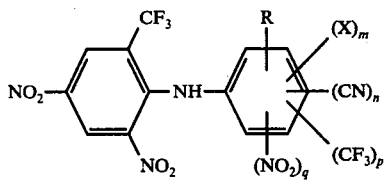

wherein R represents a hydrogen atom or an alkyl group containing up to six carbon atoms, X represents a halogen atom, m is zero or an integer from one to three, n is zero or one, p is zero, one or two and q is zero, one or two, the sum of m,n,p and q being one, two or three; provided that the group

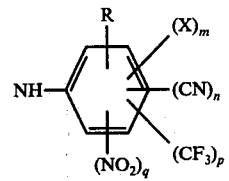

does not represent the 4-cyano-2,6-dinitroanilino group or the 4-trifluoromethyl-2,6-dinitroanilino group.

In a more preferred aspect the invention provides dinitrobenzotrifluorides of the general formula:

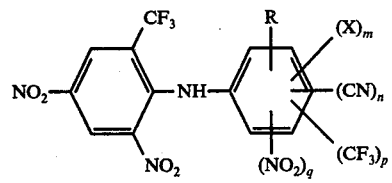

wherein R represents a hydrogen atom or an alkyl group containing up to six carbon atoms, X represents a halogen atom, m is zero or an integer from one to three, n is zero or one, p is zero, one or two and q is zero or one, the sum of m,n,p and q being one, two or three.

Particularly useful compounds are those comprising halogen atoms, trifluoromethyl or methyl groups as substituents. Thus in a yet more preferred aspect the invention provides dinitrobenzotrifluorides of the general formula:

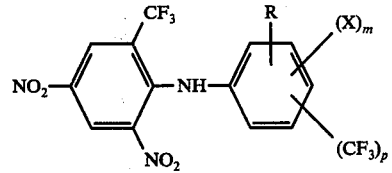

wherein R is a hydrogen atom or methyl; X is halogen and m is zero or an integer from one to three, p is zero, one or two, the sum of m and p being one, two or three. One especially preferred group of compounds within this definition is that wherein m is 1 to 3 and p is zero, and another especially preferred group of compounds within this definition is that wherein m is zero and p is one or two.

Specific dinitrobenzotrifluorides of the invention which have been found to be useful in the practice of the invention are listed in the Table 1, together with some physical characteristics for each compound, the headings to the columns of Table 1 conform to the substituent groups on the diphenylamine structure of the general formula:

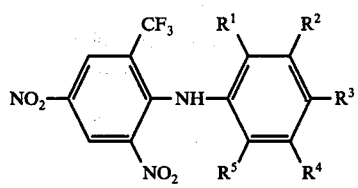

TABLE 1

| Compound No. | R¹ | R² | R³ | R⁴ | R⁵ | Melting Point °C | CALCULATED %C | %H | %N | FOUND %C | %H | %N |
|---|---|---|---|---|---|---|---|---|---|---|---|---|
| 1 | NO₂ | H | NO₂ | H | H | 182 | 37.4 | 1.4 | 16.8 | 37.9 | 1.6 | 16.8 |
| 2 | NO₂ | H | CF₃ | H | H | 137 | 38.2 | 1.4 | 12.7 | 38.3 | 1.4 | 12.7 |
| 3 | Cl | H | NO₂ | H | Cl | 164 | 35.4 | 1.1 | 12.7 | 35.5 | 1.2 | 12.5 |
| 4 | CN | H | NO₂ | H | H | 133 | 42.3 | 1.5 | 17.6 | 42.1 | 1.7 | 17.6 |
| 5 | NO₂ | H | Cl | H | H | 181 | 35.4 | 1.5 | 13.8 | 38.2 | 1.5 | 13.7 |
| 6 | NO₂ | H | NO₂ | H | Cl | 166 | 34.5 | 1.1 | 15.5 | 34.4 | 1.1 | 15.1 |
| 7 | NO₂ | H | Cl | H | Br | 170 | 32.2 | 1.0 | 11.5 | 32.0 | 1.2 | 11.4 |
| 8 | NO₂ | H | Br | H | H | 199 | 34.6 | 1.3 | 12.4 | 34.4 | 1.5 | 12.2 |
| 9 | NO₂ | H | CF₃ | H | Cl | 102 | 35.4 | 1.1 | 11.8 | 35.3 | 1.2 | 11.6 |
| 10 | NO₂ | H | Cl | H | Cl | 151 | 35.4 | 1.1 | 12.7 | 35.2 | 1.3 | 12.6 |
| 11 | NO₂ | H | Br | H | Cl | 164 | 32.2 | 1.0 | 11.5 | 32.3 | 1.1 | 11.2 |
| 12 | H | CF₃ | H | CF₃ | H | 83 | 38.9 | 1.3 | 9.1 | 38.7 | 1.3 | 9.3 |
| 13 | Cl | H | Cl | H | Cl | 105 | 36.3 | 1.2 | 9.8 | 36.5 | 1.3 | 9.9 |
| 14 | Br | H | NO₂ | H | H | 131 | 34.6 | 1.3 | 12.4 | 34.6 | 1.4 | 12.2 |
| 15 | Cl | H | H | CH₃ | H | 127 | 44.9 | 2.1 | 11.2 | 44.9 | 2.6 | 10.9 |
| 16 | Cl | H | H | Cl | H | 126 | 39.4 | 1.5 | 10.6 | 39.3 | 1.5 | 10.6 |
| 17 | Cl | H | Cl | H | H | 97 | 39.4 | 1.5 | 10.6 | 39.4 | 1.5 | 10.5 |
| 18 | H | Cl | Cl | H | H | 108 | 39.4 | 1.5 | 10.6 | 39.0 | 1.4 | 10.6 |
| 19 | H | Cl | H | Cl | H | 111 | 39.4 | 1.5 | 10.6 | 39.0 | 1.4 | 10.5 |
| 20 | Cl | H | NO₂ | H | H | 120 | 38.4 | 1.5 | 13.8 | 38.2 | 1.6 | 13.7 |
| 21 | Cl | H | H | H | Cl | 97–99 | 39.5 | 1.5 | 10.6 | 40.0 | 1.5 | 10.5 |
| 22 | Br | H | Br | H | Br | 146 | 27.7 | 0.9 | 7.5 | 27.9 | 0.9 | 7.2 |
| 23 | CF₃ | H | Cl | H | H | 157 | 39.1 | 1.4 | 9.8 | 39.0 | 1.4 | 9.7 |
| 24 | NO₂ | H | CH₃ | H | H | 180–182 | 43.6 | 2.3 | 14.5 | 43.6 | 2.4 | 14.5 |
| 25 | NO₂ | H | H | H | CH₃ | 173–175 | 43.6 | 2.3 | 14.5 | 43.4 | 2.3 | 14.5 |
| 26 | NO₂ | H | Cl | Cl | H | 151–153 | 35.4 | 1.1 | 12.7 | 35.2 | 1.2 | 12.5 |
| 27 | H | Cl | CN | H | H | 179–181 | 43.4 | 1.6 | 14.5 | 43.1 | 1.7 | 14.3 |
| 28 | H | Cl | F | H | H | 84–85 | 41.2 | 1.6 | 11.1 | 41.2 | 1.7 | 11.2 |
| 29 | H | NO₂ | Cl | H | H | 163–164 | 38.6 | 1.5 | 13.9 | 38.5 | 1.5 | 14.0 |
| 30 | Cl | H | H | NO₂ | H | 160–162 | 38.4 | 1.5 | 13.8 | 38.4 | 1.7 | 13.6 |
| 31 | H | Cl | OCH₃ | H | H | 139–142 | 42.9 | 2.3 | 10.7 | 42.9 | 2.9 | 10.7 |
| 32 | F | H | H | NO₂ | H | 134–136 | 40.0 | 1.6 | 14.4 | 40.1 | 1.6 | 14.3 |
| 33 | CH₃ | H | Cl | H | H | 146–149 | 44.8 | 2.4 | 11.2 | 45.0 | 2.5 | 11.3 |
| 34 | F | H | F | H | H | 86–89 | 42.1 | 1.7 | 11.6 | 42.0 | 1.8 | 11.3 |
| 35 | H | CF₃ | Cl | H | H | 112–113 | 39.1 | 1.4 | 9.8 | 38.7 | 1.4 | 10.0 |
| 36 | H | Cl | CH₃ | H | H | 110–111 | 44.8 | 2.4 | 11.2 | 44.6 | 2.4 | 11.0 |
| 37 | H | CF₃ | NO₂ | H | H | 144–146 | 38.2 | 1.4 | 12.7 | 38.2 | 1.4 | 12.6 |
| 38 | CH₃ | H | H | NO₂ | H | 125–126 | 43.5 | 2.3 | 14.5 | 43.7 | 2.4 | 14.7 |
| 39 | H | CH₃ | F | H | H | 95–96 | 46.8 | 2.5 | 11.7 | 46.7 | 2.5 | 11.7 |
| 40 | CH₃ | H | NO₂ | H | H | 105–109 | 43.6 | 2.3 | 14.5 | 43.3 | 2.4 | 14.4 |
| 41 | Cl | Cl | H | H | H | 91 | 39.4 | 1.5 | 10.6 | 39.2 | 1.7 | 10.5 |
| 42 | F | H | CH₃ | H | H | 86–87 | 44.8 | 2.5 | 11.7 | 44.4 | 2.4 | 11.5 |
| 43 | F | H | H | F | H | 101–104 | 43.0 | 1.7 | 11.6 | 42.9 | 1.8 | 11.6 |
| 44 | OCH₃ | H | NO₂ | H | H | 173–176 | 41.8 | 2.2 | 13.9 | 41.8 | 2.3 | 13.9 |
| 45 | Cl | H | NO₂ | Cl | H | 165–167 | 35.4 | 1.1 | 12.7 | 35.8 | 1.2 | 12.5 |
| 46 | Br | H | Br | H | H | 126–127 | 32.2 | 1.2 | 8.7 | 32.4 | 1.3 | 8.7 |
| 47 | Br | H | H | H | Br | 115–117 | 32.2 | 1.2 | 8.7 | 32.3 | 1.2 | 8.9 |
| 48 | Br | H | H | Br | H | 132 | 32.2 | 1.2 | 8.7 | 32.0 | 1.3 | 8.6 |
| 49 | NO₂ | H | H | H | H | 154–156 | 41.9 | 1.9 | 15.1 | 41.5 | 2.0 | 15.5 |
| 50 | H | H | NO₂ | H | H | 110 | 41.9 | 1.9 | 15.0 | 41.9 | 2.0 | 15.0 |
| 51 | H | H | CN | H | H | 197 | 47.7 | 2.0 | 15.9 | 47.7 | 2.0 | 15.9 |
| 52 | H | H | Cl | H | H | 104–106 | 45.1 | 1.9 | 11.6 | 45.1 | 2.1 | 12.0 |
| 53 | H | Cl | H | H | H | 122 | 45.1 | 1.9 | 11.6 | 45.2 | 2.1 | 12.0 |
| 54 | H | H | Br | H | H | 117–119 | 38.4 | 1.7 | 10.3 | 38.4 | 1.9 | 10.3 |
| 55 | Br | H | H | CF₃ | H | 132 | 35.5 | 1.3 | 8.9 | 35.7 | 1.3 | 8.7 |
| 56 | CN | H | H | H | H | 152 | 47.7 | 2.0 | 15.9 | 47.6 | 2.2 | 15.6 |
| 57 | H | Br | H | H | H | 92–93 | 38.4 | 1.7 | 10.3 | 38.4 | 1.8 | 10.5 |
| 58 | H | NO₂ | H | H | H | 194 | 42.0 | 1.9 | 15.1 | 42.0 | 1.9 | 15.3 |
| 59 | H | CN | H | H | H | 212 | 47.8 | 2.0 | 15.9 | 47.5 | 2.1 | 15.9 |
| 60 | F | H | H | H | H | 102–103 | 47.2 | 2.1 | 8.5 | 47.0 | 2.3 | 8.3 |
| 61 | H | I | H | H | H | 98–99 | 34.2 | 1.5 | 9.2 | 34.2 | 1.6 | 9.2 |
| 62 | H | H | I | H | H | 136–137 | 34.2 | 1.5 | 9.2 | 34.7 | 1.6 | 9.2 |
| 63 | Cl | H | Br | H | H | 110–112 | 35.5 | 1.4 | 9.6 | 35.6 | 1.4 | 9.6 |
| 64 | H | CH₃ | Br | H | H | 112 | 40.0 | 2.2 | 10.0 | 39.9 | 2.3 | 9.9 |
| 65 | Br | H | CH₃ | H | NO₂ | 154 | 36.1 | 1.7 | 12.0 | 36.2 | 1.7 | 12.0 |
| 66 | Cl | H | Cl | Cl | H | 124–127 | 36.3 | 1.2 | 9.8 | 36.5 | 1.3 | 9.7 |
| 67 | H | CF₃ | H | H | H | 101–103 | 42.5 | 1.8 | 10.6 | 42.4 | 2.0 | 10.5 |
| 68 | Cl | H | H | H | H | 91–94 | 43.2 | 2.0 | 11.6 | 43.2 | 2.0 | 11.4 |
| 69 | Br | H | H | H | H | 95–96 | 38.5 | 1.7 | 10.3 | 38.6 | 1.7 | 10.3 |
| 70 | CH₃ | H | F | H | H | 118–120 | 48.7 | 2.6 | 8.1 | 48.5 | 2.6 | 8.3 |
| 71 | H | CF₃ | Br | H | H | 122–124 | 35.5 | 1.3 | 8.9 | 35.2 | 1.4 | 8.7 |
| 72 | CH₃ | H | Br | H | H | 155–156 | 40.0 | 2.1 | 10.0 | 40.3 | 2.1 | 9.9 |
| 73 | CF₃ | H | H | H | H | 108–110 | 42.6 | 1.8 | 10.1 | 42.6 | 1.8 | 10.5 |
| 74 | Cl | H | CH₃ | H | H | 95–97 | 44.8 | 2.4 | 11.2 | 44.8 | 2.6 | 11.4 |
| 75 | Br | H | CH₃ | H | H | 108–109 | 40.9 | 2.1 | 10.0 | 40.1 | 2.1 | 10.2 |
| 76 | NO₂ | H | F | H | H | 141–143 | 40.0 | 1.6 | 14.4 | 40.1 | 1.7 | 14.4 |
| 77 | OCH₃ | H | H | NO₂ | H | 186 | 42.1 | 2.2 | 13.9 | 41.7 | 2.3 | 13.9 |

Of the compounds listed in Table 1, the following have been found to be exceptionally useful as acaricides or fungicides:

2-(2-chloro-5-methylanilino)-3,5-dinitrobenzotrifluoride (Compound No. 15)

2-(2,5-dichloroanilino)-3,5-dinitrobenzotrifluoride (Compound No. 16)

2-(2,6-dichloroanilino)-3,5-dinitrobenzotrifluoride (Compound No. 21)

2-(3-trifluoromethylanilino)-3,5-dinitrobenzotrifluoride (Compound No. 67)

The dinitrobenzotrifluorides according to the invention may be prepared by a variety of processes. Thus a compound of formula:

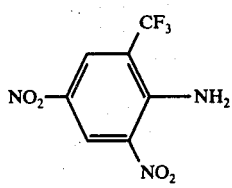

may be treated with a compound of formula:

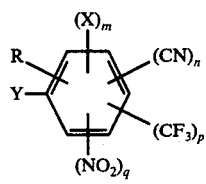

wherein Y represents a halogen atom, and R,X,$m,n,p$ and $q$ are as defined hereinabove, to obtain the dinitrobenzotrifluorides. Alternatively, the dinitrobenzotrifluorides may be prepared by treating a compound of formula:

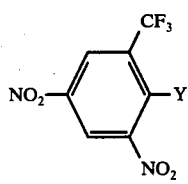

with a compound of formula:

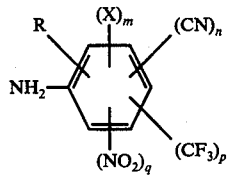

wherein R,X,Y,$m,n,p$ and $q$ are as defined herein above. These processes may in some cases be carried out by heating the reactants together in the absence of a diluent and/or a base, but preferably a solvent or diluent and a base is present. Suitable solvents include, for example, nonhydroxylic materials such as dimethylformamide, dimethylsulphoxide, sulpholane, acetonitrile and tetrahydrofuran. Of these dimethylformamide is particularly preferred. Hydroxylated solvents, for example, methanol and ethanol, may be used in certain circumstances when the presence of the hydroxyl group does not interfere with the progress of the reaction. Suitable bases include sodium hydride (although not when a hydroxylated solvent or diluent is used), alkali metal carbonates, such as potassium carbonate and alkali metal hydroxides such as potassium hydroxide. The temperature at which the reaction may be carried out will depend upon the choice of reactants, solvent or diluent and base. When dimethylformamide and sodium hydride are used the reaction generally takes place in the range −10° C. to +30° C., but higher temperatures up to 100° C. may be employed when other bases are used.

The process generally consists of dissolving or suspending the reactant bearing the amino group in a solvent or diluent in the presence of the base, allowing the base to react with the reactant by the removal of a proton from the amino group and thereafter adding the second reactant. After allowing a period of time for the reaction to occur the product may be isolated by dilution with a diluent in which the product is insoluble, usually water, which causes the product to precipitate out. The product may then be separated by filtration and recrystallised from a suitable recrystallising solvent or mixture of solvents to yield the product in a substantially pure state.

Other methods of preparation may also be used. Certain of the compounds which bear halogen substituents may be obtained by halogenation of diphenylamine derivatives already bearing the other substituents. Also those bearing nitro substituents may be obtained by the careful nitration of the appropriate diphenylamine derivatives without nitro-substituents. Again extra halo and/or nitro substituents may be introduced into compounds already bearing such substituents. These nitration and halogenation processes may be carried out in any manner well known in the art for the nitration and halogenation of benzenoid aromatic substances.

These nitration and/or halogenation steps may be carried out on diphenylamine derivatives which are outside the scope of the invention, or on diphenylamine derivatives which are already within the scope of the invention of which the following are examples:

2-trifluoromethyl-2',4,6-trinitrodiphenylamine, (m.p. 154°–156°)

2-trifluoromethyl-4,4',6-trinitrodiphenylamine, (m.p. 110°)

The intermediate diphenylamines may be made by a process similar to that outlined above for the compounds according to the invention from an appropriately substituted aniline and an appropriately substituted halobenzene.

The invention also includes pesticidal compositions comprising a dinitrobenzotrifluoride of the invention and also comprising a diluent or carrier.

In a further aspect, therefore, this invention provides a pesticidal composition comprising as an active ingredient a dinitrobenzotrifluoride having the general formula:

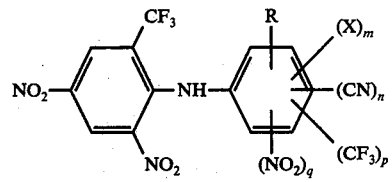

wherein R,X,$m,n,p$ and $q$ are as hereinbefore defined; and a carrier for the active ingredient.

In a preferred aspect the invention provides a pesticidal composition comprising, as an active ingredient, a dinitrobenzotrifluoride having the formula:

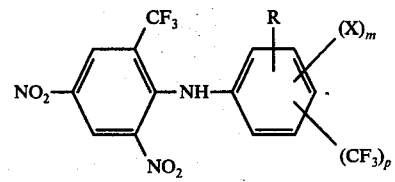

wherein R is hydrogen or methyl; X is halogen and $m$ is zero or an integer from one to three, $p$ is zero, one or two, the sum of $m$ and $p$ being one, two or three; and a carrier for the active ingredient.

In a more preferred aspect the invention provides a pesticidal composition comprising, as an active ingredient one of the dinitrobenzotrifluorides numbered 15, 16, 21 and 67 of Table 1; and a carrier for the active ingredient.

The dinitrobenzotrifluoride of this invention are preferably used in the form of compositions and these compositions may be used for agricultural and horticultural purposes. The type of composition used in any instance will depend upon the particular purpose for which it is to be used.

The compositions may be in the form of dusting powders or granules wherein the active ingredient is mixed with a solid diluent or carrier. Suitable solid diluents or carriers may be, for example, kaolin, bentonite, kieselguhr, dolomite, calcium carbonate, talc, powdered magnesia, Fuller's earth, gypsum, diatomaceous earth and China Clay. A suitable granular diluent is granulated pumice.

The compositions may also be in the form of dispersable powders or grains comprising, in addition to the active ingredient, a wetting agent to facilitate the dispersion of the powder or grains in liquids. Such powders or grains may include fillers, suspending agents and the like.

The compositions may also be in the form of liquid preparations to be used as dips or sprays which are generally aqueous dispersions or emulsions containing the active ingredient in the presence of one or more wetting agents, dispersing agents, emulsifying agents or suspending agents.

Wetting agents, dispersing agents and emulsifying agents may be of the cationic, anionic or non-ionic type. Suitable agents of the cationic type include, for example, quaternary ammonium compounds, for example, cetyltrimethyl-ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, butylnaphthalene sulphonate, and a mixture of the sodium salts of diisopropyl- and triisopropyl-naphthalene sulphonic acids. Suitable agents of the non-ionic type include, for example, the condensation products of ethylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene oxide, and the lecithins.

Suitable suspending agents are, for example, hydrophilic colloids, for example polyvinylpyrrolidone and sodium carboxymethylcellulose, and the vegetable gums, for example gum acacia and gum tragacanth.

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage to be capable of dilution with water in order to form aqueous preparations which remain homogeneous for a sufficient time to enable them to be applied by conventional spray equipment. The concentrates may conveniently contain from about 10–85% by weight of the active ingredient or ingredients and generally from about 25–60% by weight of the active ingredient or ingredients. When diluted to form aqueous preparations, such preparations may contain varying amounts of the active ingredient or ingredients depending upon the purpose for which they are to be used, but an aqueous preparation containing from between 0.001% and 0.01% up to approximately 10% by weight of active ingredient or ingredients may be used.

It is to be understood that the biologically active compositions of this invention may comprise, in addition to a dinitrobenzotrifluoride one or more other compounds having biological activity, for example, an insecticide, fungicide or acaricide. They may also incorporate one or more stabilizing agents, for example epoxides, for example epichlorhydrin.

The compositions to be used as sprays may also be in the form of aerosols wherein the formulation is held in a container under pressure in the presence of a propellant such as fluorotrichloromethane or dichlorodifluoromethane.

By the inclusion of suitable additives, for example for improving the distribution, adhesive power and resistance to rain on treated surfaces, the different compositions can be better adapted for the various uses for which they are intended.

The compounds and compositions of the invention are useful for combating pests. The term "pest" or "pests" as used in this specification and claims means invertebrate pests, particularly insect and acarine pests, and also foliar fungal pests of plants, and the meaning of "pesticidal" as used herein is similarly limited. In a further aspect therefore, the invention provides a method of combating pests which comprises applying to the pests themselves, to the locus of the pests or to the habitat of the pests a dinitrobenzotrifluoride of the present invention or a composition comprising such a dinitrobenzotrifluoride. More particularly the invention provides a method of combating pests of plants which comprises applying to the plants a compound or composition of the present invention. The application may be made to treat an infestation or infection of the plant by the pest which is already occurring, or plants which are liable to such infestation or infection may be treated prophylactically. Application may be of the undiluted chemical in certain instances but it is preferable to apply a composition, such as one of those which have been generally described hereinabove, by dusting or spraying the locus of the pests, for example the foliage of plants. The terms "plant" and "plants" as used herein are intended to mean in general economically useful plants, e.g. food and fibre crop plants or ornamental plants, but of course other types of plant may also be treated at any stage of growth from emergence to maturity, and treatment may be given to the foliage, fruit, stems, trunks or branches of the plants, as appropriate to the particular plant and pest concerned.

The compounds of the invention and compositions comprising them are very toxic to a wide variety of insect and other invertebrate pests, including, for example, the following:

*Tetranychus telarius* (red spider mites)
*Aphis fabae* (aphids)
*Megoura viceae* (aphids)

*Aedes aegypti* (mosquitos)
*Dysdercus fasciatus* (capsids)
Musca domestica (houseflies)
*Blattella germanica* (cockroaches)
*Pieris brassicae* (white butterfly, larvae)
*Plutella maculipennis* (diamond back moth, larvae)
*Phaedon cochleariae* (mustard beetle)
*Calandra granaria* (grain beetle)
*Tribolium confusum* (flour beetle)
*Agriolimax reticulatus* (slugs)

In a preferred aspect the invention provides a method of combating and controlling phytophasgous mites which comprises treating plants invested with or liable to infestation by such mites with a dinitrobenzotrifluoride of the invention or a composition thereof. Phytophagous mites are economically important pests of many crops, including, for example, cotton, citrus, apples, pears and other top fruit.

The compounds and compositions of the invention are also useful in the control of foliar fungal pests of plants, including the following:
*Puccinia recondita* (rust of wheat)
*Phytophthora infestans* (blight of tomatoes)
*Plasmopara viticola* (powdery mildew of vines)
*Uncinula necator* (downy mildew of vines)
*Piricularia oryzae* (blast of rice)
*Podosphaera leucotricha* (powdery mildew of apples)

Thus it can be seen that the invention provides the opportunity to treat a single crop for both insect and fungal pests of that crop by a single application. For example, the fungal disease *Podosphaera leucotricha* and the mite *Tetranychus telarius* both occur as pests of apple trees, and both may be combated and controlled by application of a composition incorporating an invention compound.

It is, of course, well known in the pesticide art that the application of pesticidally effective materials to plants at rates in excess of the rates necessary to provide an insecticidal, acaricidal or fungicidal effect may cause unwanted damage to the plants. The scope of this invention insofar as it relates to the application of the compounds or compositions of the invention to economically useful plants to provide a desirable pesticidal effect does not extend to application of the said compounds or compositions at rates where more than an acceptable level of unwanted damage occurs. The actual rate to be used in any particular circumstance may be readily determined by simple experimentation without the exercise of the inventive faculty and such experimentation is well within the capacity of skilled workers in the art.

Factors to be taken into consideration when determining the correct rate to be used include, the nature of the particular chemical chosen, the nature of the plant, the nature of the pest, the climatic conditions and the agricultural practice appropriate to the plant and its geographical location. A suitable rate for the treatment of mature apple trees to combat European red spider mite (*Tetranychus telarius*) is from 50 to 250 parts per million of active ingredient in a composition sprayed on at more than 100 liters per hectare.

The invention is illustrated, but not limited, by the following examples:

EXAMPLE 1

This Example illustrates the preparation of 2(2-chloro-5-methylanilino)-3,5-dinitrobenzotrifluoride, (compound No. 15 of Table 1).

Powdered potassium hydroxide (2.0 g.) was added in portions over 5 minutes to a stirred solution of 3-amino-4-chlorotoluene (2.8 g.) in dimethylformamide (15 ml.) at the ambient temperature and stirring was continued for a further 5 minutes. A solution of 2-chloro-3,5-dinitro-benzotrifluoride (5.4 g.) in dimethylformamide (15 ml.) was then added over 5 minutes, and following the addition, the mixture was stirred for 30 minutes. After acidification with concentrated hydrochloric acid the mixture was poured into water (15 ml.). The precipitated solid was separated from the supernatant liquid by decantation and recrystallised from methylated spirit to yield 2(2-chloro-5-methylanilino)-3,5-dinitrobenzotrifluoride, with a melting point of 127° C.

EXAMPLE 2

This example illustrates the preparation of 2(2,4,6-trichloroanilino)-3,5-dinitrobenzotrifluoride, (compound No. 13 of Table 1).

2,4,6-trichloroaniline (3.9 g.) was dissolved in dimethylformamide (20 ml.) and carefully added to sodium hydride (obtained by washing sodium hydride in mineral oil (2.0 g; 50%) with petrol) suspended in dimethylformamide (10 ml.) at 10° C. When the addition was complete the temperature of the mixture was allowed to rise to the ambient temperature over a period of 30 minutes, before being cooled to 10° C. A solution of 2-chloro-3,5-dinitrobenzotrifluoride (5.4 g.) in dimethylformamide (20 ml.) was slowly added, and the mixture stirred at the ambient temperature for 5 hours, and allowed to stand for further 16 hours. The mixture was poured into iced water and the resultant mixture acidified with concentrated hydrochloric acid. The precipitate was collected by decanting off the supernatant liquid and recrystallised from methylated spirit to yield 2(2,4,6-trichloroanilino)-3,5-dinitrobenzotrifluoride, melting point 105° C.

EXAMPLE 3

This Example illustrates the preparation of 2(2,6-dichloroanilino)-3,5-dinitrobenzotrifluoride, (compound No. 21 of Table 1).

2,6-dichloroaniline (360 g.) was dissolved in dimethylformamide (1.5 l.) and added to sodium hydride (obtained by washing sodium hydride in mineral oil (214 g; 50%) with petrol) suspended in dimethylformamide (4.1) at 10° C. When the addition was completed the temperature of the mixture was allowed to rise to the ambient temperature and then cooled to 10° C. A solution of 2-chloro-3,5-dinitrobenzotrifluoride (600 g.) in dimethylformamide (1.5 l.) was slowly added, and the mixture stirred at the ambient temperature for 20 hours. The mixture was poured into salt/iced water (20.1) and the resultant mixture acidified with concentrated hydrochoric acid. The precipitate was collected by decanting off the supernatant liqui and recrystallised from methylated spirit to yield 2(2,6-dichloroanilino)-3,5-dinitrobenzotrifluoride, melting point 97°–99° C.

EXAMPLE 4

This Example illustrates the preparation of 2(2-nitroanilino)-3,5-dinitrobenzotrifluoride, (compound No. 49 of Table 1).

To a stirred solution of 2-nitroaniline (6.91 g.) and 2-chloro-3,5-dinitrobenzotrifluoride (13.53 g.) in dry dimethylformamide (150 ml.) potassium hydroxide (8.0 g, pellets) was added in small portions over 15 minutes. During the addition, the temperature rose from 20° C.

to 80° C. When the addition was complete the mixture was stirred for two hours at 60° C., after which concentrated hydrochloric acid was added to acidify the mixture. Industrial methylated spirit (50 ml.) was then added and the mixture stirred for 15 minutes at the ambient temperature. The solid precipitate was collected by filtration, washed with water and dried to yield 2(2-nitroanilino)-3,5-dinitrobenzotrifluoride, melting point 154°-156° C.

EXAMPLE 5

This Example illustrated the preparation of 2(2,5-dichloroanilino)-3,5-dinitrobenzotrifluoride, (compound No. 16 of Table 1).

To a stirred solution of 2,5-dichloroaniline (1.6 g.) in dry dimethylformamide (10 ml.) potassium hydroxide (1.0 g.) was added in small portions over 5 minutes, and stirring continued for a further 15 minutes. To the resultant solution was added 2-chloro-3,5-dinitrobenzotrifluoride (2.7 g.) in small portions over 5 minutes. When the addition was complete the mixture was stirred for 30 minutes at 20° C, after which concentrated hydrochloric acid was added to acidify the mixture. Industrial methylated spirit (10 ml.) was then added, the mixture stirred for further 15 minutes and then poured into water (150 ml.) The solid precipitate was collected by filtration, washed with water and dried to yield 2(2,5-dichloroanilino)-3,5-dinitrobenzotrifluoride, melting point 125°-126° C.

EXAMPLE 6

This Example illustrates the preparation of 2(3-trifluoromethyl)-3,5-dinitrobenzotrifluoride, (compound No. 67 of Table 1).

A mixture of 2-chloro-3,5-dinitrobenzotrifluoride (119 g.(, 3-aminobenzotrifluoride (100 g.) and potassium carbonate (98 g.) were heated at 95° C. for 20 hours. The mixture was then cooled to ambient temperature, industrial methylated spirit (20 ml.) was added followed by water (200 ml.), and then acidified with concentrated hydrochloric acid to give a yellow oil, which crystallised. Recrystallisation of this solid from isopropyl alcohol gave 2(3-trifluoromethyl)-3,5-dinitrobenzotrifluoride, melting point 101°-103° C.

EXAMPLE 7

This Example illustrates the preparation of 2(4-chloroanilino)-3,5-dinitrobenzotrifluoride, (compound No. 52 of Table 1).

A mixture of 4-chloroaniline (127.5 g) and 2-chloro-3,5-dinitrobenzotrifluoride (270.5 g.) in toluene (2 l.) was heated under reflux for 16 hours and the hot mixture then filtered. The filtrate was concentrated in vacuo, and the true amounts of toluene removed by co-distillation with industrial methylated spirit, to give a black semi-solid. Extraction of this solid with cyclohexane gave yellow crystals of 2(4-chloroanilino)-3,5-dinitrobenzotrifluoride, melting point 104°-106° C.

EXAMPLE 8

By procedures similar to those illustrated in Examples 1 to 7 the following dinitrobenzotrifluorides were obtained from 2-chloro-4,6-dinitrobenzotrifluoride and the appropriately substituted aniline:

2,(2,4-dinitroanilino)-3,5-dinitrobenzotrifluoride (compound No. 1, Table 1),
2(2-nitro-4-trifluoromethylanilino)-3,5-dinitrobenzotifluoride (compound No. 2, Table 1),
2(2,6-dichloro-4-nitroanilino)-3,5-dinitrobenzotrifluoride (compound No. 3, Table 1),
2(2-cyano-4-nitroanilino)-3,5-dinitrobenzotrifluoride (compound No. 4, Table 1),
2(4-chloro-2-nitroanilino)-3,5-dinitrobenzotrifluoride (compound No. 5, Table 1),
2(6-chloro-2,4-dinitroanilino)-3,5-dinitrobenzotrifluoride (compound No. 6, Table 1),
2(6-bromo-4-chloro-2-nitroanilino)-3,5-dinitrobenzotrifluoride (compound No. 7, Table 1),
2(4-bromo-2-nitroanilino)-3,5-dinitrobenzotrifluoride (compound No. 8, Table 1),
2(6-chloro-2-nitro-4-trifluoromethylanilino)-3,5-dinitrobenzotrifluoride (compound No. 9, Table 1),
2(4,6-dichloro-2-nitroanilino)-3,5-dinitrobenzotrifluoride (compound No. 10, Table 1),
2(4-bromo-6-chloro-2-nitroanilino)-3,5-dinitrobenzotrifluoride (compound No. 11, Table 1),
2(3,5-bistrifluoromethylanilino)-3,5-dinitrobenzotrifluoride (compound No. 12, Table 1),
2(2-bromo-4-nitroanilino)3,5-dinitrobenzotrifluoride (compound No. 14, Table 1),
2(2,4-dichloroanilino)-3,5-dinitrobenzotrifluoride (compound No. 17, Table 1),
2(3,4-dichloroanilino)-3,5-dinitrobenzotrifluoride (compound No. 18, Table 1),
2(3,5-dichloroanilino)-3,5-dinitrobenzotrifluoride (compound No. 19, Table 1),
2(2-chloro-4-nitroanilino)-3,5-dinitrobenzotrifluoride (compound No. 20, Table 1),
2(2,4,6-tribromoanilino)-3,5-dinitrobenzotrifluoride (compound No. 22, Table 1),
2(4-chloro-2-trifluoromethylanilino)-3,5-dinitrobenzotrifluoride (compound No. 23, Table 1),
2(4-methyl-2-nitroanilino)-3,5-dinitrobenzotrifluoride (compound No. 24, Table 1),
2(6-methyl-2-nitroanilino)-3,5-dinitrobenzotrifluoride (compound No. 25, Table 1),
2(4,5-dichloro-2-nitroanilino)-3,5-dinitrobenzotrifluoride (compound No. 26, Table 1),
2(3-chloro-4-cyanoanilino)-3,5-dinitrobenzotrifluoride (compound No. 27, Table 1),
2(3-chloro-4-fluoroanilino)-3,5-dinitrobenzotrifluoride (compound No. 28, Table 1),
2(4-chloro-3-nitroanilino)-3,5-dinitrobenzotrifluoride (compound No. 29, Table 1),
2(2-chloro-5-nitro anilino)-3,5-dinitrobenzotrifluoride- (compound No. 30, Table 1)
2(3-chloro-5-methoxyanilino)-3,5-dinitrobenzotrifluoride- (compound No. 31, Table 1),
2(2-fluoro-5-nitroanilino)-3,5-dinitrobenzotrifluoride- (compound No. 32, Table 1),
2(4-chloro-2-methylanilino)-3,5-dinitrobenzotrifluoride- (compound No. 33, Table 1),
2(2,4-difluoroanilino)-3,5-dinitrobenzotrifluoride- (compound No. 34, Table 1),
2(4-chloro-3-trifluoromethylanilino)-3,5-dinitrobenzotrifluoride- (compound No. 35, Table 1),
2(3-chloro-4-methylanilino)-3,5-dinitrobenzotrifluoride- (compound No. 36, Table 1),
2(4-nitro-3-trifluoromethylanilino)-3,5-dinitrobenzotrifluoride- (compound No. 37, Table 1),
2(2-methyl-5-nitroanilino)-3,5-dinitrobenzotrifluoride- (compound No. 38, Table 1),
2(4-fluoro-3-methylanilino)-3,5-dinitrobenzotrifluoride- (compound No. 39, Table 1),
2(2-methyl-4-nitroanilino)-3,5-dinitrobenzotrifluoride- (compound No. 40, Table 1), 2(2,3-dichloroanilino)-3,5-dinitrobenzotrifluoride- (compound No. 41, Table 1),
2(2-fluoro-4-methylanilino)-3,5-dinitrobenzotrifluoride- (compound No. 42, Table 1),
2(2,5-difluoroanilino)-3,5-dinitrobenzotrifluoride- (compound No. 43, Table 1),
2(2-methoxy-4-nitroanilino)-3,5-dinitrobenzotrifluoride- (compound No. 44, Table 1),
2(2,5-dichloro-4-nitroanilino)-3,5-dinitrobenzotrifluoride- (compound No. 45, Table 1),
2(2,4-dibromoanilino)-3,5-dinitrobenzotrifluoride- (compound No. 46, Table 1),
2(2,6-dibromoanilino)-3,5-dinitrobenzotrifluoride- (compound No. 47, Table 1),
2(2,5-dibromoanilino)-3,5-dinitrobenzotrifluoride- (compound No. 48, Table 1),
2(4-nitroanilino)-3,5-dinitrobenzotrifluoride- (compound No. 50, Table 1),
2(4-cyanoanilino)-3,5-dinitrobenzotrifluoride- (compound No. 51, Table 1),
2(3-chloroanilino)-3,5-dinitrobenzotrifluoride- (compound No. 53, Table 1),
2(4-bromoanilino)-3,5-dinitrobenzotrifluoride- (compound No. 54, Table 1),
2(2-bromo-5-trifluoromethylanilino)-3,5-dinitrobenzotrifluoride- (compound No. 55, Table 1),
2(2-cyanoanilino)-3,5-dinitrobenzotrifluoride- (compound No. 56, Table 1),
2(3-bromoanilino)-3,5-dinitrobenzotrifluoride- (compound No. 57, Table 1),
2(3-nitroanilino)-3,5-dinitrobenzotrifluoride- (compound No. 58, Table 1),
2(3-cyanoanilino)-3,5-dinitrobenzotrifluoride- (compound No. 59, Table 1),
2(2-fluoroanilino)-3,5-dinitrobenzotrifluoride- (compound No. 60, Table 1),
2(3-iodoanilino)-3,5-dinitrobenzotrifluoride- (compound No. 61, Table 1),
2(4-iodoanilino)-3,5-dinitrobenzotrifluoride- (compound No. 62, Table 1),
2(4-bromo-2-chloroanilino)-3,5-dinitrobenzotrifluoride- (compound No. 63, Table 1),
2(4-bromo-3-methylanilino)-3,5-dinitrobenzotrifluoride- (compound No. 64, Table 1),
2(2-bromo-4-methyl-6-nitroanilino)-3,5-dinitrobenzotrifluoride- (compound No. 65, Table 1),
2(2,4,5-trichloroanilino)-3,5-dinitrobenzotrifluoride- (compound No. 66, Table 1),
2(2-chloroanilino)-3,5-dinitrobenzotrifluoride- (compound No. 68, Table 1),
2(2-bromoanilino)-3,5-dinitrobenzotrifluoride- (compound No. 69, Table 1),
2(4-fluoro-2-methylanilino)-3,5-dinitrobenzotrifluoride- (compound No. 70, Table 1),
2(4-bromo-3-trifluoromethylanilino)-3,5-dinitrobenzotrifluoride- (compound No. 71, Table 1),
2(4-bromo-2-methylanilino)-3,5-dinitrobenzotrifluoride- (compound No. 72, Table 1),
2(2-trifluoromethylanilino)-3,5-dinitrobenzotrifluoride- (compound No. 73, Table 1),
2(2-chloro-4-methylanilino)-3,5-dinitrobenzotrifluoride- (compound No. 74, Table 1),
2(2-bromo-4-methylanilino)-3,5-dinitrobenzotrifluoride- (compound No. 75, Table 1),
2(4-fluoro-2-nitroanilino)-3,5-dinitrobenzotrifluoride- (compound No. 76, Table 1),
2(2-methoxy-5-nitroanilino)-3,5-dinitrobenzotrifluoride- (compound No. 77, Table 1).

EXAMPLE 9

5 parts by weight of 2(2-chloro-5-methylanilino)-3,5-dinitrobenzotrifluoride (compound No. 15, Table 1), were thoroughly mixed in a suitable mixer with 95 parts by weight of talc. There was thus obtained a dusting powder.

EXAMPLE 10

10 parts by weight of 2(2,5-dichloroanilino)-3,5-dinitrobenzotrifluoride (compound No. 16 of Table 1), 10 parts of an ethylene oxide-octyl phenol condensate ("Lissapol" NX: "Lissapol" is a Trade Mark) and 80 parts by weight of diacetone alcohol were thoroughly mixed. There was thus obtained a concentrate which, on mixing with water, gave an aqueous dispersion suitable for application as a spray in the control of insect pests.

EXAMPLE 11

A granular composition was prepared by dissolving the active ingredient in a solvent, spraying the solution obtained on to granules of pumice and allowing the solvent to evaporate.

|  | % wt. |
|---|---|
| 2(2,6-dichloroanilino)-3,5-dinitrobenzotrifluoride- (compound No. 21, Table 1). | 5.0 % |
| Pumice granules | 95.0 % |
|  | 100.0 % |

EXAMPLE 12

An aqueous dispersion formulation was prepared by mixing and grinding the ingredients recited below in the proportions stated.

|  | % wt. |
|---|---|
| 2(2,5-dichloroanilino)-3,5-dinitrobenzotrifluoride- (compound No. 16, Table 1). | 40.0 % |
| Calcium lignosulphonate | 10.0 % |
| Water | 50.0 % |
|  | 100.0 % |

EXAMPLE 13

An emulsifiable concentrate was made up by mixing together the ingredients set out below in the proportions stated and stirring the mixture until all the constituents were dissolved.

|  | % wt. |
|---|---|
| 2(3-trifluoromethylanilino)-3,5-dinitrobenzotrifluoride- (compound No. 67, Table 1). | 10.0 % |
| Ethylene Dichloride | 40.0 % |
| Calcium dodecylbenzene-sulphonate | 5.0 % |
| "Lubrol" L | 10.0 % |
| "Aromasol" H | 35.0 % |
|  | 100.0 % |

EXAMPLE 14

A composition in the form of grains readily dispersible in a liquid, e.g. water, was prepared by grinding together the first three of the ingredients listed below in the presence of added water and then mixing in the sodium acetate. The resultant mixture was dried and passed through a British Standard mesh sieve, size 44-100, to obtain the desired size of grains.

|  | % wt. |
|---|---|
| 2(2,5-dichloroanilino)-3,5-dinitrobenzotrifluoride (compound No. 16, Table 1) | 50.0 % |
| "Dispersol" T | 25.0 % |
| "Lubrol" APN 5 | 1.5 % |
| Sodium acetate | 23.5% |
|  | 100.0 % |

EXAMPLE 15

The ingredients listed below were ground together in the proportions stated by weight to produce a powder formulation readily dispersable in liquids.

|  | % wt. |
|---|---|
| 2(2,5-dichloroanilino)-3,5-dinitrobenzotrifluoride (compound No. 16, Table 1) | 45.0 % |
| "Dispersol" T | 5.0 % |
| "Lissapol" NX | 0.5 % |
| "Cellofas" B 600 | 2.0 % |
| Sodium acetate | 47.5% |
|  | 100.0 % |

EXAMPLE 16

A col formulation (a col formulation is a suspension of finely divided particles in which the mean particle diameter is less than about 3 microns), was prepared by ball-milling the constituents in the amounts set out by weight below, and then forming an aqueous suspension of the ground mixture with water.

|  | % wt. |
|---|---|
| 2(2-nitroanilino)-3,5-dinitrobenzotrifluoride (compound No. 49, Table 1) | 40.0 % |
| "Dispersol" T | 10.0 % |
| "Lubrol" L | 1.0 % |
| Water | 49.0 % |
|  | 100.0 % |

EXAMPLE 17

A dispersible powder formulation was made by mixing together the ingredients in amounts by weight set out below and then grinding the mixture until all the constituents were thoroughly mixed.

|  | % wt. |
|---|---|
| 2(2,6-dichloroanilino)-3,5-dinitrobenzotrifluoride (compound No. 21, Table 1) | 25.0 % |
| "Aerosol" OT/B | 2.0 % |
| "Dispersol" AC | 5.0 % |
| China Clay | 28.0 % |
| Silica | 40.0 % |
|  | 100.0 % |

EXAMPLE 18

This example illustrates the preparation of two dispersible powder formulations. In each instance all the ingredients are mixed in the proportions (by weight) stated and the mixture then ground in a comminution mill.

|  | % wt. |
|---|---|
| 2(3-trifluoromethylanilino)-3,5-dinitrobenzotrifluoride (compound No. 67, Table 1) | 25.0 % |
| "Perminal" BX | 1.0 % |
| "Dispersol" T | 5.0 % |
| Polyvinylpyrrolidone | 10.0 % |
| Silica | 25.0 % |
| China Clay | 34.0 % |
|  | 100.0 % |

EXAMPLE 19

The ingredients set out below were formulated into a dispersible powder by mixing and grinding the ingredients in the proportions stated.

|  | % wt. |
|---|---|
| 2(2-chloro-5-methylanilino)-3,5-dinitrobenzotrifluoride (compound No. 15, Table 1) | 25.0 % |
| "Aerosol" OT/B | 2.0 % |
| "Dispersol" AC | 5.0 % |
| China Clay | 68.0 % |
|  | 100.0 % |

By procedures similar to those illustrated in Examples 9 to 19 corresponding pesticidal compositions incorporating as active ingredients any of the other compounds set out in Table 1 may be prepared.

The following constitutes an explanation of the compositions or substances represented by the various Trade Marks and Trade Names referred to in the foregoing Examples.

| "LUBROL" L | is a condensate of 1 mole of nonyl phenol with 13 molar proportions of ethylene oxide. |
|---|---|
| "AROMASOL" H | is a solvent mixture of alkyl-benzenes |
| "DISPERSOL" T and AC | is a mixture of sodium sulphate and a condensate of formaldehyde with the sodium salt of naphthalene sulphonic acid. |
| "LUBROL" APN 5 | is a condensate of 1 mole of nonyl phenol with 5½ moles of naphthalene oxide. |
| "CELLOFAS" B 600 | is a sodium carboxymethyl cellulose thickener. |
| "LISSAPOL" NX | is a condensate of 1 mole of nonyl phenol with 8 moles of ethylene oxide. |
| "AEROSOL" OT/B | is dioctyl sodium sulphosuccinate. |
| "PERMINAL" BX | is an alkyl naphthalene sulphonate (sodium salt) |

EXAMPLE 20

The activity of the dinitrobenzotrifluorides of the present invention was shown in tests against a variety of insect and other invertebrate pests. The compound was used in the form of a liquid preparation containing 0.1% by weight of the compound except in the tests with *Aedes aegypti* where the preparations contained 0.01% by weight of the compounds. The preparations were made by dissolving the compounds in a mixture of solvents consisting of 4 parts by volume of acetone and 1 part by volume of diacetone alcohol. The solutions were then diluted with water containing 0.01% by weight of a wetting agent sold under the trade name "LISSAPOL" NX until the liquid preparations contained the required concentration of the compound. "Lissapol" is a Trade Mark.

The test procedure adopted with regard to each pest was basically the same and comprised supporting a number of pests on a medium which was usually a host plant or a foodstuff on which the pests feed, and treating either or both the pests and the medium with the preparations.

The mortality of the pests was then assessed at periods usually varying from one to three days after the treatment.

The results of the tests are given below in Table 2. In this table the first column indicates the name of the pest species.

Each of the subsequent columns indicates the host plant or medium on which it was supported, the number of days which were allowed to elapse after the treatment before assessing the mortality of the pests, and the results obtained for each compound. The assessment is expressed in integers which range from 0-3.

0 represents less than 30% kill
1 represents 30–49% kill
2 represents 50–90% kill
3 represents over 90% kill In the Table 2 "contact test" indicates that both the pests and the medium were treated, "residual test" indicates that the medium was treated before infestation with the pests.

TABLE 2

| Pest species | Support medium | No. of Days | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|---|---|
| *Aphis fabae* (green aphids) | Broad bean | 2 | 0 | 3 | 0 | 0 | 0 | 0 | 0 | 3 | 3 | 3 | 3 | 3 | 2 | 3 | 2 | 0 | 3 | 3 | 3 | 3 | 3 | 3 |
| *Megoura viceae* (black aphids) | Broad bean | 2 | 0 | 3 | 0 | 0 | 0 | 0 | 0 | 3 | 3 | 3 | 3 | 3 | 3 | 3 | 3 | 3 | 3 | 3 | 3 | 3 | 3 | 3 |
| *Aedes aegypti* (mosquito adults) | Plywood | 1 | 0 | 2 | 0 | 0 | 0 | 0 | 0 | 0 | 0 | 0 | 0 | 3 | 3 | 0 | 0 | 0 | 3 | 0 | 0 | 3 | 3 | 3 |
| *Musca domestica* (houseflies - contact test) | Milk/sugar | 2 | 3 | 3 | 3 | 1 | 3 | 3 | 3 | 3 | 3 | 3 | 2 | 3 | 3 | 3 | 0 | 3 | 3 | 3 | 3 | 3 | 3 | 3 |
| *Musca domestica* (houseflies - residual test) | Plywood | 2 | 0 | 3 | 0 | 0 | 0 | 0 | 0 | 0 | 0 | 2 | 1 | 3 | 0 | 0 | 0 | 0 | 2 | 2 | 3 | 1 | 0 | 0 |
| *Pieris brassicae* (cabbage white caterpillars) contact test | Cabbage | 2 | 3 | 3 | 3 | 3 | 2 | 3 | 2 | 2 | 3 | 3 | 3 | 3 | 3 | 3 | 3 | 3 | 3 | 3 | 3 | 3 | 3 | 3 |
| *Plutella maculipennis* (diamond back moth, larvae), contact test | Mustard | 2 | 1 | 3 | 0 | 1 | 3 | 2 | 2 | 2 | 0 | 0 | 2 | 3 | 0 | 0 | 2 | 3 | 1 | 3 | 0 | 0 | 3 | 0 |
| *Phaedon cochleariae* (mustard beetles) - residual test | Mustard | 2 | 2 | 2 | 2 | 0 | 0 | 0 | 3 | 0 | 0 | 2 | 1 | 3 | 2 | 3 | 0 | 0 | 2 | 1 | 1 | 2 | 2 | 1 |
| *Blattella germanica* (cockroaches) | — | 1 | 0 | 3 | 0 | 0 | 2 | 0 | 0 | 2 | 2 | 1 | 0 | 3 | 3 | 0 | 0 | 3 | 3 | 0 | 3 | 3 | 3 |
| *Meloidogyne incognita* (nematodes) | Water | 1 | 3 | 3 | 3 | 3 | 3 | 3 | 3 | 3 | 3 | 3 | 3 | 3 | 3 | 3 | — | — | — | — | — | — | — | — |
| *Aedes aegypti* (mosquito larvae) | Water | 1 | 3 | 3 | 3 | 3 | 3 | 3 | 3 | 3 | 3 | 3 | 3 | 3 | 3 | 3 | 3 | 3 | 3 | 3 | 3 | 3 | 3 | 3 |
| *Dysdercus fasciatus* (capsid) | Grain | 2 | 0 | 3 | 0 | 0 | 0 | 2 | 3 | 0 | 3 | 2 | 3 | 3 | 0 | 3 | 0 | 0 | 3 | 0 | 3 | 3 | 3 | 1 |

| Pest Species | Support medium | No. of days | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|
| *Aphis fabae* (green aphids) | Broad bean | 2 | 3 | 2 | 0 | 3 | 3 | 2 | 0 | 3 | 0 | 3 | 0 | 3 | 3 | 0 | 2 | 2 | 0 | 3 | 3 | 0 | 3 | 3 |
| *Megoura viceae* (black aphids) | Broad bean | 2 | 3 | 1 | 0 | 3 | 2 | 3 | 0 | 3 | 0 | 3 | 0 | 3 | 3 | 0 | 2 | 2 | 0 | 3 | 3 | 0 | 3 | 2 |
| *Aedes aegypti* (mosquito adults) | Plywood | 1 | 3 | 0 | 0 | 3 | 0 | 2 | 0 | 0 | 0 | 0 | 0 | 3 | 3 | 0 | 0 | 0 | 0 | 3 | 3 | 2 | 3 | 0 |
| *Musca domestica* (houseflies - contact test) | Milk/sugar | 2 | 3 | 0 | 2 | 3 | 3 | 3 | 3 | 3 | 0 | 3 | 3 | 3 | 3 | 0 | 3 | 3 | 3 | 3 | 3 | 2 | 3 | 3 |
| *Musca domestica* (houseflies - residual test) | Plywood | 2 | 3 | 0 | 0 | 0 | 0 | 3 | 0 | 0 | 0 | 0 | 0 | 0 | 3 | 0 | 0 | 0 | 0 | 3 | 0 | 0 | 3 | 0 |
| *Pieris brassicae* (cabbage white caterpillars) contact test | Cabbage | 2 | 3 | 0 | 3 | 3 | 2 | 3 | 3 | 3 | 2 | 3 | 3 | 3 | 3 | 3 | 3 | 3 | 3 | 3 | 3 | 0 | 3 | 3 |
| *Plutella maculipennis* (diamond back moth larvae) contact test | Mustard | 2 | 3 | 0 | 0 | 0 | 0 | 0 | 0 | 2 | 1 | 1 | 2 | 3 | 2 | 0 | 2 | 2 | 0 | 3 | 3 | 0 | 3 | 3 |
| *Phaedon cochleariae* (mustard beetles)- residual test | Mustard | 2 | 3 | 0 | 0 | 0 | 1 | 2 | 3 | 3 | 2 | 0 | 0 | 0 | 3 | 1 | 2 | 2 | 0 | 3 | 3 | 0 | 3 | 2 |
| *Blattella germanica* (cockroaches) | — | 1 | 3 | 0 | 0 | 3 | 1 | 3 | 3 | 2 | 0 | 0 | 0 | 1 | 3 | 0 | 0 | 0 | 0 | 3 | 3 | 2 | 3 | 0 |
| *Meloidogyne incognita* (nematodes) | Water | 1 | — | 0 | 3 | — | — | — | 3 | 3 | 0 | 0 | 3 | 0 | — | 0 | 3 | 3 | 3 | 3 | 3 | 2 | 3 | 3 |
| *Aedes aegypti* (mosquito larvae) | Water | 1 | 3 | 0 | 3 | 3 | 3 | 3 | 3 | 3 | 0 | 3 | 3 | 3 | 3 | 3 | 0 | 0 | 0 | 3 | 0 | 0 | 3 | 0 |
| *Dysdercus fasciatus* (capsid) | Grain | 2 | 1 | 0 | 0 | 0 | 0 | 3 | 0 | 0 | 0 | 0 | 0 | 0 | 0 | 0 | 3 | 3 | 3 | 3 | 3 | 0 | 3 | 3 |

| Pest species | Support medium | No. of days | 45 | 46 | 47 | 48 | 49 | 50 | 51 | 52 | 53 | 54 | 55 | 56 | 57 | 58 | 59 | 60 | 61 | 62 | 63 | 64 | 65 | 66 |
|---|---|---|---|---|---|---|---|---|---|---|---|---|---|---|---|---|---|---|---|---|---|---|---|---|
| *Aphis fabae* (green aphids) | Broad beans | 2 | 3 | 3 | 3 | 3 | 0 | 3 | 0 | 0 | 0 | 0 | 3 | 3 | 2 | 2 | 0 | 3 | 0 | 0 | 3 | 0 | 3 | 3 |
| *Megoura viceae* | Broad | | | | | | | | | | | | | | | | | | | | | | | |

TABLE 2-continued

| Pest Species | Support medium | No. of days | | | | | | | | | | | | | | | | | | | | | | |
|---|---|---|---|---|---|---|---|---|---|---|---|---|---|---|---|---|---|---|---|---|---|---|---|---|
| (black aphids) | beans | 2 | 3 | 3 | 3 | 3 | 0 | 3 | 0 | 0 | 0 | 0 | 3 | 3 | 2 | 3 | 0 | 0 | 0 | 0 | 3 | 0 | 3 | 3 |
| Aedes aegypti (mosquito adults) | Plywood | 1 | 0 | 0 | 3 | 1 | 0 | 0 | 0 | 0 | 2 | 0 | 3 | 0 | 0 | 0 | 0 | 0 | 2 | 0 | 3 | 0 | 0 | 3 |
| Musca domestica (houseflies - contact test) | Milk/sugar | 2 | 3 | 3 | 3 | 3 | 3 | 3 | 3 | 3 | 3 | 3 | 3 | 0 | 3 | 3 | 2 | 3 | 2 | 3 | 3 | 0 | 0 | 3 |
| Musca domestica (houseflies) residual test | Plywood | 2 | 0 | 0 | 0 | 0 | — | — | — | — | — | — | 3 | 0 | 0 | 0 | 0 | 0 | 0 | 3 | 2 | 0 | 0 | 3 |
| Pieris brassicae (cabbage white caterpillar) contact test | Cabbage | 2 | 2 | 3 | 3 | 3 | 3 | 3 | 3 | 3 | 3 | 3 | 3 | 3 | 3 | 3 | 3 | 3 | 0 | 0 | 3 | 0 | 0 | 3 |
| Plutella maculipennis (diamond back moth, larvae) contact test | Mustard | 2 | 3 | 3 | 3 | 3 | 2 | 0 | 0 | 0 | 0 | 1 | 2 | 0 | 2 | 0 | 0 | 0 | — | 0 | 0 | 0 | 0 | 2 |
| Phaedon cochleariae (mustard beetles-residual test) | Mustard | 2 | 3 | 3 | 3 | 3 | 2 | 0 | 2 | 3 | 0 | 2 | 1 | 3 | 1 | 1 | 0 | 0 | 2 | 1 | 1 | 0 | 0 | 0 |
| Blattella germanica (cockroaches) | — | 1 | 0 | 0 | 3 | 1 | 0 | 3 | 0 | 3 | 0 | 3 | 0 | 0 | 0 | 0 | 0 | 0 | 0 | 3 | 3 | 0 | 0 | 3 |
| Meloidogyne incognita (nematodes) | Water | 1 | 3 | 3 | 3 | 3 | 3 | 0 | — | — | — | — | — | 0 | 3 | — | — | — | — | 3 | — | 0 | 3 | — |
| Aedes aegypti (mosquito larvae) | Water | 1 | 0 | 0 | 0 | 0 | 2 | 3 | 3 | 3 | 3 | 3 | 3 | 3 | 3 | 2 | 2 | 0 | 3 | 3 | 3 | 3 | 3 | 3 |
| Dysdercus fasciatus (capsids) | Grain | 2 | 2 | 3 | 3 | 3 | — | — | — | — | — | 3 | 0 | 0 | 0 | 0 | 0 | 0 | 0 | 1 | 0 | 0 | 2 | |

| Pest Species | Support medium | No. of days | Compound No. (table 1) | | | | | | | | | | |
|---|---|---|---|---|---|---|---|---|---|---|---|---|
| | | | 67 | 68 | 69 | 70 | 71 | 72 | 73 | 74 | 75 | 76 | 77 |
| Aphis fabae (green aphids) | Broad bean | 2 | 3 | 3 | 3 | 3 | 3 | 3 | 3 | 1 | 2 | 3 | 0 |
| Megoura viceae (black aphids) | Broad bean | 2 | 3 | 3 | 3 | 3 | 3 | 3 | 3 | 0 | 1 | 3 | 0 |
| Aedes aegypti (mosquito adults) | Plywood | 1 | 3 | 0 | 2 | 0 | 3 | 0 | 3 | 0 | 0 | 0 | 0 |
| Musca domestica (houseflies) contact test | Milk/sugar | 2 | 3 | 3 | 3 | 1 | 3 | 3 | 3 | 0 | 1 | 3 | 3 |
| Musca domestica (houseflies) residual test | Plywood | 2 | 1 | 0 | 0 | 0 | 2 | 0 | 0 | 0 | 0 | 3 | 0 |
| Pieris brassicae (cabbage white caterpillar) contact test | cabbage | 2 | 3 | 3 | 3 | 3 | 3 | 3 | 3 | 2 | 3 | 2 | 0 |
| Plutella maculipennis (diamond back moth, larvae) contact test | Mustard | 2 | 0 | 0 | 0 | 0 | 0 | 0 | 1 | 0 | 0 | 2 | 0 |
| Phaedon cochleariae (mustard beetles) residual test | Mustard | 2 | 0 | 0 | 0 | 0 | 0 | 1 | 0 | 0 | 0 | 0 | 0 |
| Blattella germanica (cockroaches) | — | 1 | 0 | 0 | 0 | 0 | 3 | 0 | 0 | 0 | 0 | 0 | 0 |
| Meloidogyne incognita (nematodes) | Water | 1 | — | — | — | — | — | — | — | 3 | 0 | — | 3 |
| Aedes aegypti (mosquito larvae) | Water | 1 | 3 | 2 | 3 | 3 | 3 | 3 | 3 | 2 | 1 | 3 | 0 |
| Dysdercus fasciatus (capsids) | Grain | 2 | 0 | 0 | 0 | 0 | 3 | 0 | 0 | 0 | 0 | 0 | 0 |

In a similar test compounds Nos. 12 and 13 were shown to be toxic to grain weevils (*Calandra granaria*) and compound Nos. 2, 9, 10, 11, 13, 28, 35 and 37 were shown to be toxic to flour beetles (*Tribolium confusum*).

EXAMPLE 21

Compounds of the invention were tested for molluscicidal activity and details of the tests conducted are as follows.

A weighed sample of the compound under test was dissolved in 0.5 cc. of an ethanol and acetone mixture (50:50 v/v). The solution was diluted with 0.5 cc. of water and poured onto a calf feeding pellet in a glass petri dish and the pellet was air dried for 24 hours. The weight of compound used was chosen so that the dried pellet contained 4% by weight of the active ingredient. Two replicates each consisting of a plastic petri dish containing a pellet, 2 slugs, and a moistened filter paper to maintain a high relative humidity were used in each test. The dishes were left in the cold room (10° C.). After six days the kill was assessed.

The slugs used were *Agriolimax reticulatus* (Mull), and they had been starved for 24 hours before the commencement of the tests. The results of the test are set out in Table 3 below.

TABLE 3

| Compound No. (Table 1) | % kill of slugs | Compound No. (Table 1) | % kill of slugs |
|---|---|---|---|
| 3 | 50 | 27 | 100 |
| 9 | 100 | 28 | 50 |
| 13 | 75 | 29 | 50 |
| 14 | 50 | 35 | 100 |
| 16 | 50 | 37 | 50 |
| 20 | 50 | 41 | 50 |
| 21 | 100 | 46 | 50 |
| 22 | 50 | 63 | 50 |
| 23 | 75 | 66 | 100 |
| 26 | 50 | | |

EXAMPLE 22

This example illustrates the favourable level on control of both organo-phosphorus susceptible and resistant strains of the European red-spider mite (*Tetranychus telarius*) by the compounds of the present invention. Both adult mites and mite ova were used. French bean plants at the primary leaf stage were infested with mites and sprayed with compositions containing the invention compounds at a variety of rates. Table 4 gives the lowest rate of application (in parts per million of compound in the composition used) sufficient to give complete control. The mortality of the mites was assessed three days after the spraying took place.

In the test with mite ova the mortality of the ova (i.e., failure to hatch) was assessed 6 days after spraying the plants. Immediately before spraying the adults present on the leaf were removed by subjecting the leaf surface to an air blast. The mite ovicidal results are given in Table 4.

TABLE 4

| Compound No. Table 1 | Lowest concentration (ppm) giving 100% mortality | | Compound No. Table 1 | Lowest concentration (ppm) giving 100% mortality | |
|---|---|---|---|---|---|
| | Adults | Eggs | | Adults | Eggs |
| 1 | 1000 | N.A. | 21 | 2.5 | 2.5 |
| 2 | 50 | 50 | 22 | 25 | 25 |
| 3 | 1000 | N.A. | 23 | 2.5 | 2.5 |
| 4 | 100 | N.A. | 24 | 1000 | 1000 |
| 5 | 1000 | 1000 | 25 | 100 | 1000 |
| 6 | 1000 | 1000 | 26 | 12.5 | 12.5 |
| 7 | 250 | N.A. | 27 | 200 | 1000 |
| 8 | 250 | 250 | 28 | 10 | 10 |
| 9 | 250 | 250 | 29 | 1000 | 1000 |
| 10 | 62.5 | 62.5 | 30 | 250 | 250 |
| 11 | 100 | 100 | 32 | 50 | 1000 |
| 12 | 10 | 10 | 33 | 10 | 10 |
| 13 | 5 | 5 | 34 | 25 | 25 |
| 14 | 25 | 25 | 35 | 5 | 5 |
| 15 | 50 | 50 | 36 | 1000 | 1000 |
| 16 | 2.5 | 2.5 | 37 | 250 | 250 |
| 17 | 12.5 | 12.5 | 38 | 50 | 50 |
| 18 | 2.5 | 2.5 | 39 | 1000 | N.A. |
| 19 | 10 | 10 | 40 | 100 | 100 |
| 20 | 50 | 50 | 41 | 50 | 50 |
| 42 | 1000 | 1000 | | | |
| 43 | 200 | 200 | 61 | 1000 | 1000 |
| 44 | 1000 | 1000 | 62 | 50 | 50 |
| 46 | 12.5 | 12.5 | 63 | 2.5 | 2.5 |
| 47 | 10 | 10 | 64 | <200 | <200 |
| 48 | 25 | 25 | 65 | 62.5 | 62.5 |
| 49 | 50 | 250 | 66 | 10 | 10 |
| 50 | 50 | 50 | 67 | 12.5 | 12.5 |
| 51 | 10 | 1000 | 68 | 50 | 50 |
| 52 | 50 | 50 | 69 | 12.5 | 50 |
| 53 | 250 | 1000 | 70 | 12.5 | 1000 |
| 54 | 50 | 50 | 71 | 2.5 | 2.5 |
| 55 | <62.5 | <1000 | 72 | 25 | 1000 |
| 56 | 50 | 50 | 73 | 10 | 10 |
| 57 | 250 | 250 | 74 | 250 | N.A. |
| 58 | 50 | N.A. | 75 | 200 | N.A |
| 59 | 50 | 200 | 76 | 12.5 | 200 |
| 60 | 50 | 1000 | 77 | 62.5 | 250 |

Note: "N.A." in Table 4 indicates that no activity was observed at the highest rate used (1000 p.p.m.)

EXAMPLE 23

This example illustrates the superior acaricidal properties of the 2-anilino-3,5-dinitrobenzotrifluorides of the present invention in comparison with the isomeric 4-anilino-3,5-dinitrobenzotrifluorides disclosed in Belgian patent 808,918. The tests were carried out in the manner of Example 22 and the results are given in Table 5 for each pair of isomers.

TABLE 5

| Name of Compound | Lowest Concentration (ppm) giving 100% mortality. | |
|---|---|---|
| | Adults | Eggs |
| 2(2-nitro-4-trifluoromethylanilino)-3,5-dinitrobenzotrifluoride | 50 | 50 |
| 4(2-nitro-4-trifluoromethylanilino)-3,5-dinitrobenzotrifluoride | N.A. | N.A. |
| 2(2,6-dichloroanilino)-3,5-dinitrobenzotrifluoride | 2.5 | 2.5 |
| 4(2,6-dichloroanilino)-3,5-dinitrobenzotrifluoride | N.A. | N.A. |
| 2(3,4-dichloroanilino)-3,5-dinitrobenzotrifluoride | 2.5 | 2.5 |
| 4(3,4-dichloroanilino)-3,5-dinitrobenzotrifluoride | N.A. | N.A. |
| 2(2,4,5-trichloroanilino)-3,5-dinitrobenzotrifluoride | 62.5 | 62.5 |
| 4(2,4,5-trichloroanilino)-3,5-dinitrobenzotrifluoride | N.A. | N.A. |
| 2(4-bromo-2-nitroanilino)-3,5-dinitrobenzotrifluoride | 250 | 250 |
| 4(4-bromo-2-nitroanilino)-3,5-dinitrobenzotrifluoride | N.A. | N.A. |
| 2(2-bromo-4-nitroanilino)-3,5-dinitrobenzotrifluoride | 25 | 25 |
| 4(2-bromo-4-nitroanilino)-3,5-dinitrobenzotrifluoride | N.A. | N.A. |
| 2(2-chloro-4-trifluoromethylanilino)-3,5-dinitrobenzotrifluoride | 2.5 | 2.5 |
| 4(2-chloro-4-trifluoromethylanilino)-3,5-dinitrobenzotrifluoride | N.A. | N.A. |
| 2(2-chloro-4-nitroanilino)-3,5-dinitrobenzotrifluoride | 50 | 50 |
| 4-(2-chloro-4-nitroanilino)-3,5-dinitrobenzotrifluoride | N.A. | N.A. |
| 2(2,4,6-trichloroanilino)-3,5-dinitrobenzotrifluoride | 5 | 5 |
| 4(2,4,6-trichloroanilino)-3,5-dinitrobenzotrifluoride | 62.5 | N.A. |

TABLE 5-continued

| Name of Compound | Lowest Concentration (ppm) giving 100% mortality. | |
|---|---|---|
|  | Adults | Eggs |
| 2(3,5-bistrifluoromethyl-anilino)-3,5-dinitrobenzo-trifluoride | 10 | 10 |
| 4(3,5-bistrifluoromethyl-anilino)-3,5-dinitrobenzo-trifluoride | 250 | N.A. |

Note: "N.A." in Table 5 indicates that no activity was observed at the highest rate used (1000 p.p.m.)

The results in Table 5 clearly indicate that for each pair of isomers tested the 2-isomer is markedly superior than the known 4-isomer.

EXAMPLE 24

This example illustrates the comparative acaricidal properties of a number of commercially important known acaricidal products. These are (a) 2,2,2-trichloro-1,1-di(4-chlorophenyl)ethanol (I), also known by its British Standard common name of dicofol and sold under the Trade Mark "Kelthane"; (b) tricyclohexyltin hydroxide (II), sold under the Trade Mark "Plictran"; (c) 2,4,4',5-tetrachlorodiphenyl sulphone (III), also known by its British Standards common name of tetradifon and sold under the Trade Mark "Tedion"; (d) S(3,4-dihydro-4-oxobenzo[d][1,2,3]-triazin-3-ylmethyl) dimethyl phosphorothiolothionate (IV), also known by its International Standard common name of azinphos-methyl, and sold under the Trade Mark "Gusathion".

The test was carried out in the manner of Example 22 and the results are given below in Table 6.

TABLE 6

| Known compound | Lowest concentration (p.p.m) giving 100% mortality. | |
|---|---|---|
|  | Adults | Eggs |
| I-dicofol | 25 | 1000 |
| II-tricyclohexyltin hydroxide | 30 | 30 |
| III-tetradifon | 1000 | 12.5 |
| IV-azinphos-methyl | 50* | N.A. |

Notes:
"N.A." in Table 6 indicates that no activity was observed at the highest rate used (1000 p.p.m.).
*Organo-phosphorus susceptible mites only - no activity on resistant mites.

Thus it can be seen by a comparison of the results set out in Table 4 and Table 6 that the compounds of the present invention have for the most part at least comparable activity to known commercial acaricides and that several of the invention compounds are more active than the known commercial acaricides.

EXAMPLE 25

A series of field experiments was carried out to compare the acaricidal effect of certain of the invention compounds with that produced by the commercial product tricyclohexyltin hydroxide (sold under the Trade Mark "Plictran". "Plictran" is a recommended treatment for the control of phytophagous mites).

In each experiment mature fruiting apple trees were sprayed at high volume (i.e. greater than 100 liters/hectare) with a dispersible powder formulation dispersed in water. The leaves of the trees were then visually inspected at intervals and the percentage mortality of the phytophagous mites (principally Tetranychus spp.) calculated. The results are given in Tables 7 and 8.

TABLE 7

FIELD EXPERIMENT No. 1 VALENCIA, SPAIN, 1974.
% reduction in pre-spray population of spider mites.

| Compound No. (Table 1) | Rate of application p.p.m. (ai) | Days after treatment before assessment | | |
|---|---|---|---|---|
|  |  | 7 | 13 | 20 |
| 16 | 200 | 99 | 98 | 89 |
|  | 100 | 98 | 91 | 89 |
| 21 | 200 | 99 | 99 | 95 |
|  | 100 | 98 | 96 | 90 |
| "Plictran" | 200 | 96 | 94 | 93 |
|  | 100 | 78 | 65 | 80 |
| Control |  | 0 | 0 | 5 |

TABLE 8

FIELD EXPERIMENT NO. 2 FERRARA, ITALY, 1974.
% reduction in pre-spray population of spider-mites.

| Compound No. (Table 1) | Rate of application p.p.m. (ai) | Days after treatment before assessment | | | |
|---|---|---|---|---|---|
|  |  | 10 | 17 | 26 | 31 |
| 16 | 200 | 79 | 86 | 90 | 93 |
| 21 | 100 | 56 | 51 | 59 | 84 |
| "Plictran" | 200 | 39 | 70 | 66 | 67 |

Assessment of egg numbers, where these were counted, followed the same pattern as that of adult mite numbers. Microscopic examinations of eggs 13 days after treatment showed a high proportion (50–100%) to be non-viable, but replication of the samples observed was insufficient to be able to distinguish between chemical treatments.

EXAMPLE 26

This Example shows the persistence of effect (% mortality) of certain dinitrobenzotrifluorides of the invention against untreated *Pieris brassicae* larvae on cabbage plants and untreated *Plutella maculipennis* on mustard plants, each plant having been sprayed with a composition comprising a compound of the invention before infestation with the larvae.

TABLE 9

| Compound No. (Table 1) | Application rate p.p.m. (ai) | Days persistance for 100% mortality of | |
|---|---|---|---|
|  |  | *Pieris brassicae* | *Plutella maculipennis* |
| 16 | 500 | 3 | 1 |
|  | 250 | 2 | 1 |
| 21 | 500 | 3 | 8 |
|  | 250 | 3 | 1 |

EXAMPLE 27

This Example illustrates the level of control of aphids *Myzus persicae* by several compounds of the invention.

Adult female *M. persicae* on Chinese cabbage plants were sprayed with a composition comprising a compound of the invention under a modified Potter Tower. After spraying, the aphids were transferred to open plastic-coatedglass rings. The results are given in Table 10.

TABLE 10

| Compound No. (Table 1) | Application rate p.p.m. (ai) | 21 hour assessment (%) | | |
|---|---|---|---|---|
|  |  | Dead | Affected | Healthy |
| 16 | 200 | 52 | 28 | 20 |
|  | 100 | 62 | 28 | 10 |
|  | 50 | 47 | 22 | 31 |
| 21 | 200 | 68 | 26 | 6 |
|  | 100 | 53 | 40 | 7 |
|  | 50 | 53 | 27 | 20 |
| Control | — | 14 | 0 | 86 |

EXAMPLE 28

The compounds of this invention were tested against a variety of foliar fungal diseases of plants. In the test, a composition comprising an aqueous solution or suspension of the test compounds was sprayed on to the foliage of uninfected plants; the soil in which the plants were growing was also drenched with the composition. The compositions used for spraying and drenching contained 100 parts per million (p.p.m.) of the test compound except where otherwise stated in the tables of results given below. After spraying and drenching, the plants were then exposed to infection with the diseases it was desired to control, along with control plants not treated with the compound. After a period of days, depending upon the particular disease, the extent of the disease was visually assessed, as a percentage of the disease established upon the control plants which had not been treated with the compound under test, according to the grading scheme below.

| Grading | Amount of disease as a percentage of disease on control plants. |
|---|---|
| 0 | 61 to 100 |
| 1 | 26 to 60 |
| 2 | 6 to 25 |
| 3 | 0 to 5 |
| 4 | No disease |

In Table 11 the disease is given in the first column and in the second column is given the time which elapsed between infecting the plants and assessing the amount of disease.

TABLE 11

| Disease and Plant | Time Interval (days) | Disease code letter (Table 12) |
|---|---|---|
| *Puccinia recondita* (wheat) | 10 | A |
| *Phytophthora infestans* (tomato) | 3 | B |
| *Plasmopara viticola* (vine) | 7 | C |
| *Uncinula necator* (vine) | 10 | D |
| *Piricularia oryzae* (rice) | 7 | E |
| *Podosphaera leucotricha* (apple) | 10 | F |

The test results are given in Table 12 below.

TABLE 12

| Compound No. (Table 1) | A | B | C | D | E | F |
|---|---|---|---|---|---|---|
| 2 | 3 | 0 | 3 | 3 | 3 | — |
| 3 | 1 | 2 | 3 | 3 | 0 | 0 |
| 4 | 0 | 2 | 3 | 0 | 0 | — |
| 5 | 3 | 3 | 3 | 0 | 0 | — |
| 7 | 2 | 3 | 3 | 3 | 0 | — |
| 8 | 3 | 2 | 3 | 0 | 0 | — |
| 9 | 3 | 2 | 3 | 3 | — | — |
| 10 | 3 | 0 | 3 | 3 | — | + |
| 11 | 3 | 0 | 3 | 3 | — | — |
| 12 | 3 | — | 3 | 3 | — | 3 |
| 14 | 0 | — | 3 | 1 | — | — |
| 15 | 3 | 1 | 3 | 3 | 3 | 3 |
| 16 | 3 | + | 3 | 3 | 0 | 3 |
| 17 | 0 | + | — | — | 3 | 4 |
| 22 | 4 | + | 0 | 4 | 3 | 4 |
| 23 | 3 | + | 4 | 4 | 0 | 3 |
| 25 | 2 | 3 | 4 | 4 | 0 | 0 |
| 26 | 2 | 3 | 4 | 4 | 0 | 3 |
| 27 | 0 | 3 | 4 | 2 | + | 0 |
| 28 | 0 | + | + | + | + | 3 |
| 29 | 3 | 3 | 3 | — | + | 0 |
| 30 | + | 3 | 3 | 0 | 4 | — |

TABLE 12-continued

| Compound No. (Table 1) | A | B | C | D | E | F |
|---|---|---|---|---|---|---|
| 33 | — | 4 | 1 | — | — | 4 |
| 34 | 0 | 0 | 4 | — | — | 0 |
| 35 | + | + | 3 | 1 | + | 4 |
| 36 | 3 | 3 | 4 | 0 | 3 | 2 |
| 37 | 2 | 4 | 4 | — | + | 0 |
| 38 | 2 | + | 4 | 3 | 2 | 2 |
| 39 | 1 | 4 | 3 | — | 0 | 3 |
| 41 | 2 | + | 3 | — | 0 | 3 |
| 42 | 0 | 3 | 3 | — | 0 | 0 |
| 43 | 0 | + | 4 | — | 0 | 3 |
| 44 | 0 | 4 | 3 | — | 0 | 1 |
| 45 | 0 | 3 | 4 | 3 | 0 | 0 |
| 46 | 2 | 0 | 4 | 2 | 1 | 4 |
| 47 | 2 | + | 4 | 4 | 2 | 3 |
| 48 | 2 | + | 4 | 4 | 1 | 2 |
| 49 | 3 | 0 | 3 | 0 | 3 | — |
| 50 | 3 | — | 4 | + | 4 | 1 |
| 51 | — | — | 4 | — | 3 | — |
| 52 | 0 | + | 3 | 2 | 0 | 3 |
| 53 | 0 | 3 | 3 | 1 | 0 | 3 |
| 54 | 0 | 0 | 4 | 3 | 0 | 0 |
| 56 | 0 | 3 | 3 | 3 | — | 2 |
| 57 | 3 | + | 3 | — | 0 | 3 |
| 58 | 0 | 3 | 4 | — | 0 | 0 |
| 59 | — | 3 | 4 | — | — | — |
| 60 | 2 | 0 | 4 | — | 0 | 0 |
| 62 | 0 | 3 | 4 | — | 0 | 0 |
| 63 | 2 | + | 4 | — | 0 | 3 |
| 65 | 0 | 0 | 4 | — | 0 | 3 |
| 66 | 2 | + | + | — | 3 | 3 |
| 71 | 0 | — | 4 | — | 0 | 4 |
| 72 | 0 | 4 | 3 | — | 0 | 3 |
| 76 | 1 | 4 | 3 | — | 2 | 3 |

"—" denotes no result was obtained.

A number of the compounds of the invention gave excellent control, at much lower rates of application, of some of the foliar fungal diseases named hereinabove. These results are given in Table 13.

TABLE 13

| Compound No. (Table 1) | Application rate (p.p.m.) | A | C | D | F |
|---|---|---|---|---|---|
| 1 | 5 | — | 4 | — | — |
|   | 10 | 2-3 | 4 | — | — |
| 15 | 2.5 | — | 4 | — | — |
| 21 | 50 | — | 4* | — | 4* |
|    | 25 | — | 4* | — | 4 |
|    | 5 | — | 4 | — | 4 |
| 25 | 10 | — | 3-4 | — | — |
| 27 | 10 | — | 3-4 | — | — |
| 29 | 10 | — | 4 | — | — |
| 33 | 10 | — | 4 | — | 3 |
|    | 2.5 | — | 4 | — | — |
| 34 | 25 | — | 4 | — | — |
| 36 | 10 | — | 3-4 | — | — |
| 38 | 2.5 | — | 4 | — | — |
| 41 | 50 | — | 4* | — | — |
| 41 | 10 | — | 4 | — | 4 |
|    | 2.5 | — | 4 | — | 2 |
| 48 | 50 | — | 4 | 4* | 4* |
|    | 25 | — | 4 | 3-4 | 3 |
|    | 5 | — | 3-4 | — | — |
| 52 | 50 | — | 4 | — | 4* |
|    | 10 | — | 4 | — | 4 |
|    | 2.5 | — | 4 | — | 1 |
| 53 | 50 | — | 4 | 2-3* | — |
|    | 10 | — | 4 | 1-3 | — |
|    | 5 | — | 4 | 1-2 | — |
| 56 | 10 | — | 4 | — | — |
| 59 | 10 | — | 4 | — | — |

*denotes eradicant action and "—" denotes not tested.

In Table 12 above "+" indicates that a meaningful assessment of the fungicidal effect was not possible because some unwanted damage occured to the plants under test.

We claim:

1. A 2-anilino-3,5-dinitrobenzotrifluoride of the formula:

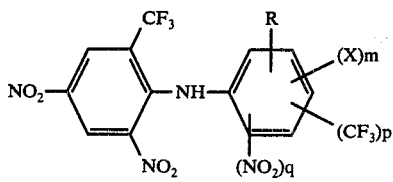

wherein R is hydrogen, methyl or methoxy;
X is halogen,
m is zero, one, when a further substitutent in addition to hydrogen is present on the ring, two or three,
p is zero, one or two,
q is zero or one
and the sum of m, p and q is one, two or three.

2. The 2-anilino-3,5-dinitrobenzotrifluoride according to claim 1 of the formula:

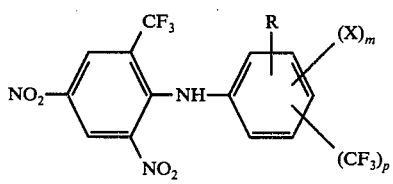

wherein R is hydrogen or methyl,
X is halogen,
m is zero, one, when a further substituent in addition to hydrogen is present on the ring, two or three,
p is zero, one or two,
and the sum of m and p is one, two or three.

3. The 2-anilino-3,5-dinitrobenzotrifluoride according to claim 2 wherein m is one, two or three, and p is zero.

4. The 2-anilino-3,5-dinitrobenzotrifluoride according to claim 2 wherein m is zero and p is one or two.

5. The 2-anilino-3,5-dinitrobenzotrifluoride selected from the group consisting of:
2(2,5-dichloroanilino)-3,5-dinitrobenzotrifluoride,
2(2,6-dichloroanilino)-3,5-dinitrobenzotrifluoride,
2(2-chloro-5-methylanilino)-3,5-dinitrobenzotrifluoride and
2(3-trifluoromethylanilino)-3,5-dinitrobenzotrifluoride.

6. A composition suitable for use in combating insect and acarine pests of plants comprising an insecticidally and acaricidally effective amount of a 2-anilino-3,5-dinitrobenzotrifluoride according to claim 1 in association with an agriculturally and horticulturally acceptable carrier.

7. The composition according to claim 6 wherein the 2-anilino-3,5-dinitrobenzotrifluoride is selected from the group consisting of:
2(2,5-dichloroanilino)-3,5-dinitrobenzotrifluoride,
2(2,6-dichloroanilino)-3,5-dinitrobenzotrifluoride,
2(2-chloro-5-methylanilino)-3,5-dinitrobenzotrifluoride, and
2(3-trifluoromethylanilino)-3,5-dinitrobenzotrifluoride.

8. The composition according to claim 6 additionally comprising a wetting agent.

9. A method of combating insect and acarine pests of plants which comprises applying to the plants an insecticidally and acaricidally effective amount of a composition according to claim 6.

10. A method of combating insect and acarine pests of plants which comprises applying to the plants an insecticidally and acaricidally effective amount of a compound of the formula:

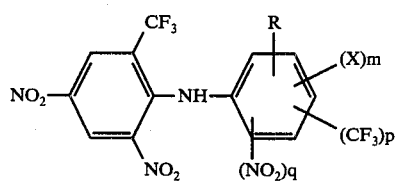

wherein R is hydrogen, methyl or methoxy;
X is halogen,
m is zero, one, two or three,
p is zero, one or two,
q is zero or one
and the sum of m, p and q is one, two or three.

* * * * *